(12) United States Patent
Reider

(10) Patent No.: US 6,924,411 B2
(45) Date of Patent: Aug. 2, 2005

(54) PRINTABLE BANDAGE

(75) Inventor: Barry James Reider, Loveland, CO (US)

(73) Assignee: Hewlett-Packard Development Company, L.P., Houston, TX (US)

(*) Notice: Subject to any disclaimer, the term of this patent is extended or adjusted under 35 U.S.C. 154(b) by 89 days.

(21) Appl. No.: 10/161,149

(22) Filed: May 31, 2002

(65) Prior Publication Data

US 2003/0225353 A1 Dec. 4, 2003

(51) Int. Cl.[7] ............................................. A61F 13/00
(52) U.S. Cl. ............................ 602/58; 602/41; 602/42
(58) Field of Search .................... 602/41–59; D24/89, D24/189; 206/440, 441; 604/304–308; 128/889, 888

(56) References Cited

U.S. PATENT DOCUMENTS

| | | | | |
|---|---|---|---|---|
| 2,292,995 A | * | 8/1942 | Greenwoll | 602/42 |
| 5,333,753 A | * | 8/1994 | Etheredge | 221/33 |
| 5,637,080 A | * | 6/1997 | Geng | 602/58 |
| D408,540 S | | 4/1999 | Dunshee et al. | |
| D433,139 S | | 10/2000 | Brogden et al. | |
| 6,512,160 B1 | * | 1/2003 | Rutsky | 602/41 |
| 2002/0064619 A1 | * | 5/2002 | Schroeder | 428/40.1 |

* cited by examiner

*Primary Examiner*—Kim M. Lewis

(57) ABSTRACT

A printable bandage system including a non-stick sheet and at least one bandage removably secured to the non-stick sheet. The bandage includes a printable portion configured to receive the printing of an image thereon.

10 Claims, 4 Drawing Sheets

PRINTABLE BANDAGE

THE FIELD OF THE INVENTION

The present invention relates to bandages and in particular to printable bandages.

BACKGROUND OF THE INVENTION

The entertainment industry has spread its reach to virtually every aspect of life. Previously mundane objects such as bandages now bear graphic images such as Mickey Mouse® characters from Disney®. Decorated bandages are fun for kids and can help kids overcome fear and discomfort associated with an injury covered by the decorated bandages. However, large media conglomerates, in cooperation with bandage manufacturing companies, exclusively control which images are carried on the bandages.

SUMMARY OF THE INVENTION

In one embodiment, the present invention provides a printable bandage system which includes a non-stick sheet and at least one bandage removably secured to the non-stick sheet. The bandage includes a printable portion configured to receive the printing of an image thereon.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
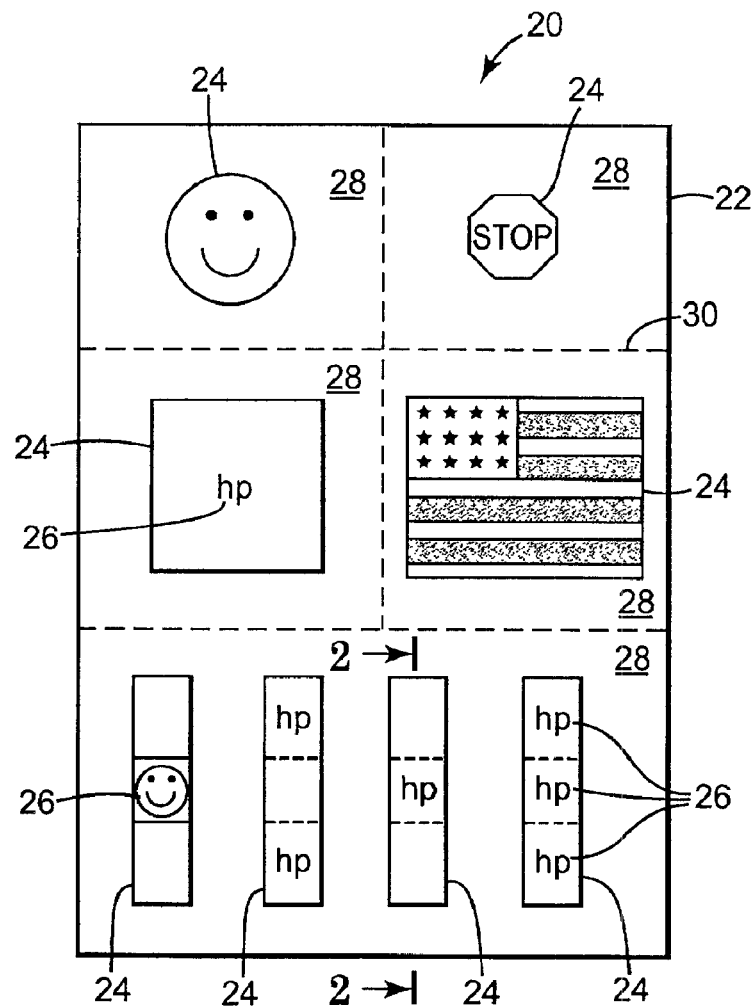
FIG. 1 is a plan view of a sheet of printable bandages, according to an embodiment of the present invention.

As shown in FIG. 1, printable bandage system 20 includes sheet 22 and a plurality of bandages 24. Each bandage 24 includes graphic image 26 as a decoration on bandage 24. Sheet 22 is divided into separable portions 28 by perforations 30. Bandages 24 are aligned on sheet 22 in a suitable arrangement to permit printing of graphic images 26 on bandages 24 as sheet 22 is fed through a printer. Graphic images 26 are not limited to the images shown in FIG. 1, but rather include any graphic image capable of being rendered and produced by a printer onto a sheet such as sheet 22 bearing bandages 24. After printing, one or more bandages 24 can be peelingly removed from sheet 22 for use to cover a wound.

Figure 2:
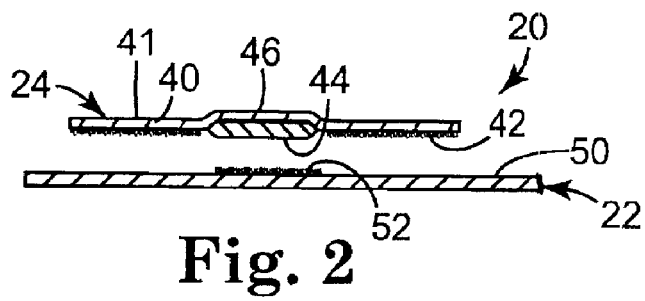
FIG. 2 is a sectional view of FIG. 1 as taken along lines 2—2, according to an embodiment of the present invention.

FIG. 2 is a sectional view of bandage 24 and a portion of sheet 22 in FIG. 1 as taken along lines 2—2. As shown in FIG. 2, bandage 24 includes protective backing 40 having non-adhesive side 41 and adhesive side 42, pad 44, graphic image 46. Sheet 22 includes nonstick surface 50 and optional adhesive portion 52. Backing 40 preferably includes any type of backing, fabric, or material suitable for use in bandages, in which all or part of backing 40 is flexible, semi-flexible, and/or rigid. Adhesive side 42 preferably includes a pressure sensitive adhesive applied to backing 40. Non-adhesive side 41 of bandage 24 includes a printable material that is suitable for receiving graphic image 46 from a printer, such as an ink jet printer, laser printer, or other type of printer capable of printing images on sheets. The printable material may comprise all or part of non-adhesive side 41.

Pad 44 preferably includes any pad used in bandages such as a gauze-like material, whether absorbent or non-absorbent, and that is secured to backing 40.

Non-stick surface 50 of sheet 22 preferably is made from a non-stick coating so that upon application of adhesive side 42 of bandage 24, bandage 24 is releasably secured to non-stick surface 50 of sheet 22. This arrangement permits bandage 24 to be peeled off from sheet 22 when desired. Optional adhesive portion 52 is provided on sheet 22 when it is desired to removably secure pad 44 against sheet 22. However, this is not normally necessary because bandage 24 typically is sufficiently secured with adhesive side 42 against sheet 22.

Figure 3:
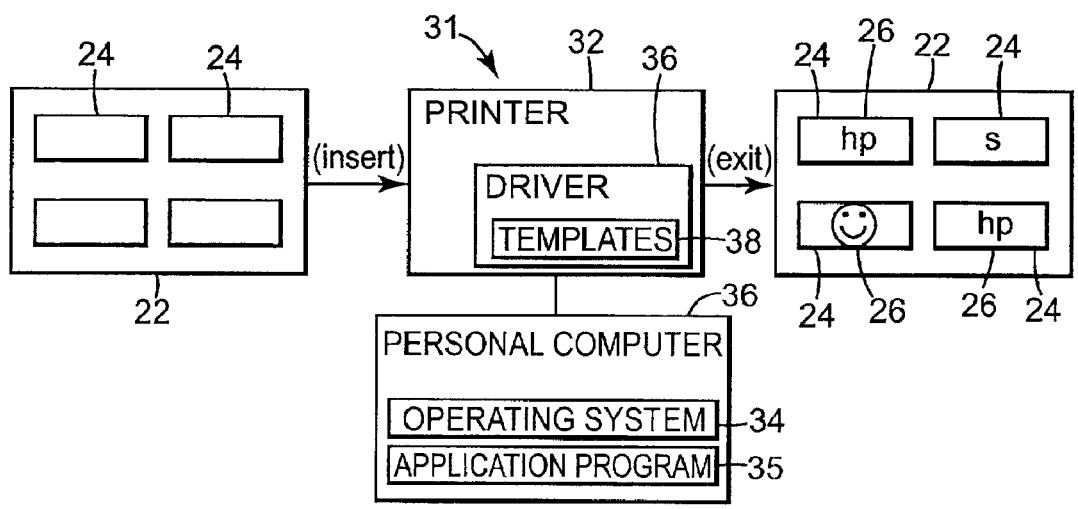
FIG. 3 is a plan view of a bandage printing system, according to an embodiment of the present invention.

FIG. 3 illustrates a bandage printing system 31 of the present invention. As shown in FIG. 3, sheet 22 having unprinted bandages 24 is fed into printer 32. Using an operating system 34 and/or application program 35 of personal computer 36, printer 32 is commanded to print image 26 onto sheet 22 in printer 32. Accordingly, printer 32 uses sheet 22 for the target of the printing job, and prints image 26 onto bandages 24 at the proper locations. Printer 32, operating system 34, and/or application program 35 includes driver 36 or other software containing the appropriate templates 38 to target printing of images 26 to the proper location on sheets 22 of printable bandages 24.

After printing images onto bandages 24, printer 32 ejects sheet 22 with printed bandages 24 from printer 32. Next, at a desired time, the consumer peelingly removes one or more bandages 24 from sheet 22 for placement on a wound. Since the printed image 26 is on non-adhesive side 41 of each bandage 24, upon application of bandage 24 to a wound, bandage 24 will display printed image 26.

With the exception of copyrighted material, a consumer has unlimited freedom to print virtually any image 26 onto the bandages. With advent of digital photography, consumer could even print images 26 such as photographs of family, places, pets, etc. onto bandages. This could personalize bandages to bear an image 26 (such as a photo) of the wearer of bandage as well as an image 26 of a mother or father of the wearer of bandage.

Figure 4:
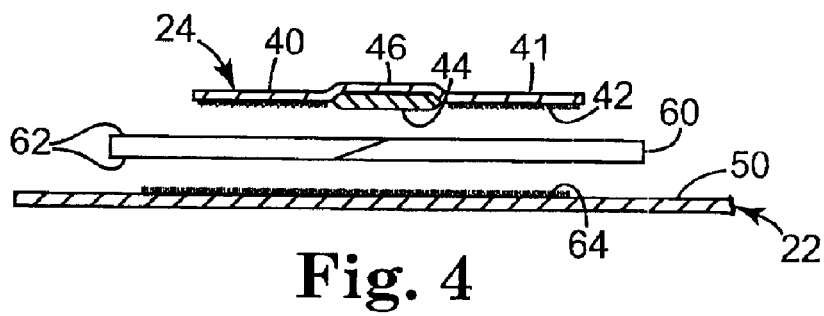
FIG. 4 is an alternative sectional view of FIG. 1 as taken along lines 2—2, according to an embodiment of the present invention.

As shown in FIG. 4, system 20 optionally includes nonstick sheet separator 60 having two opposed non-stick surfaces 62. Sheet 22 further includes adhesive portion 64 sized to correspond to size of sheet separator 60. Separator 60 optionally is inserted between sheet 22 and bandage 24 so that bandage 24 can be removed from sheet 22 with separator 60 on bandage 24 so that separator 60 provides a protective material over pad 44 and adhesive side 42 of bandage 24. This arrangement protects bandage 24 for use until a later time, while permitting removal of bandage 24 from sheet 22 after printing image 26 on bandage 24.

Figure 5:
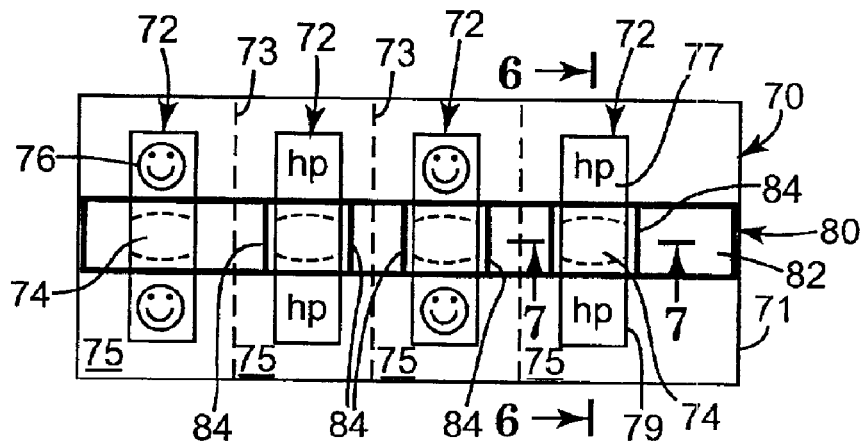
FIG. 5 is a plan view of a sheet of printable bandages, according to an embodiment of the present invention.

FIG. 5 illustrates another embodiment of the present invention in which cover 80 sealingly covers at least a portion of bandage(s) 72 to maintain sterility and/or cleanliness of bandages 72 before, during, and after printing. As shown in FIG. 5, system 70 includes sheet 71 and a plurality of bandages 72 with each bandage 72 including pad 74 and graphic image 76. Sheet 71 and bandages 72 have substantially the same features and attributes as sheet 22 and bandages 24, as previously described in association with FIGS. 1–4. For example, bandage 72 includes non-adhesive side 77 and adhesive side 78 (shown in Fig. 6), and sheet 71 includes perforations 73. Perforations 73 allow separation of portions 75 of sheet 71 so that each bandage 72 can be removed with its associated portion of sheet 71 without disturbing other bandages 72 on that sheet 71.

System 70 further comprises cover 80 including body 82 and seams 84. Cover 80 conveniently extends in a strip across all pads 74 of bandages 72. Cover 80 is provided for sealing pad 74 of bandages 72 from unwanted elements such as dust, germs, etc. In addition, cover 80 protects pad 74 and maintains the sterility of bandages 72 during printing of images 76 onto bandages 72 as sheet 71 passes through a printer. Cover 80 includes the same perforations 73 shown in sheet 71 so that each bandage 72 with sheet 71 and its portion of cover 80 can be separated from other bandages 72 for individual use.

Figure 6:
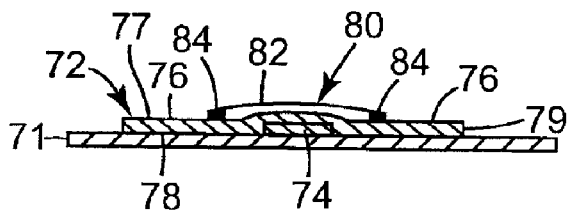
FIG. 6 is a sectional view of FIG. 5 as taken along lines 6—6, according to an embodiment of the present invention.
Figure 7:
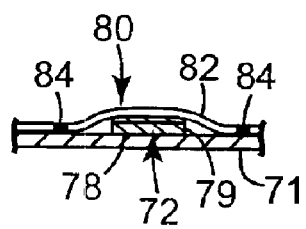
FIG. 7 is a sectional view of FIG. 5 as taken along lines 7—7, according to an embodiment of the present invention.

FIG. 6 is sectional view of FIG. 5. As shown in FIG. 6, seams 84 extend along non-adhesive side 77 of bandage 72 on opposite sides of pad 74. FIG. 7 is a sectional view of FIG. 5. As shown in FIG. 7, seams 84 extend along opposite sides of edge 79 of bandage 72. Accordingly, pad 74 of each bandage 72 is protected by cover 80 sealed by seams 84 against both sheet 71 and non-adhesive sides 77 of bandages 72.

Figure 8:
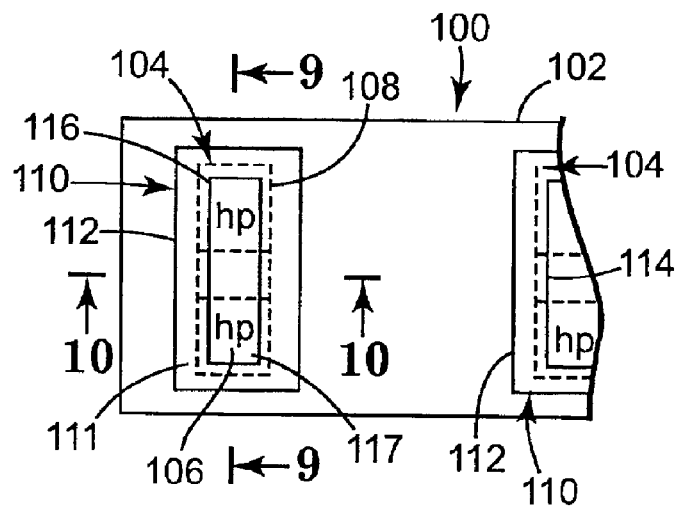
FIG. 8 is a plan view of a sheet of printable bandages, according to an embodiment of the present invention.
Figure 9:
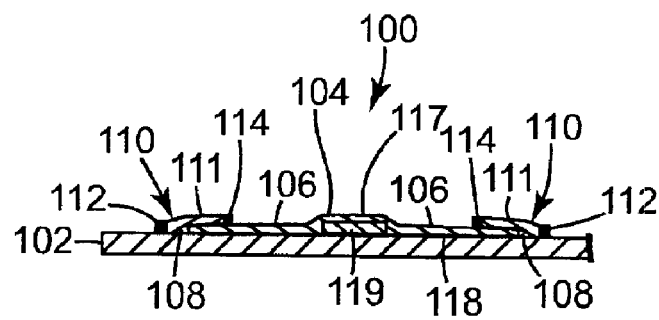
FIG. 9 is a sectional view of FIG. 8 as taken along lines 9—9, according to an embodiment of the present invention.
Figure 10:
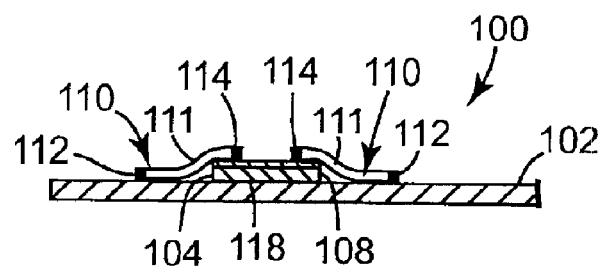
FIG. 10 is a sectional view of FIG. 8 as taken along lines 10—10, according to an embodiment of the present invention.

FIGS. 8–10 illustrate another embodiment of the present invention including a cover 110. As shown in FIG. 8, system 100 includes sheet 102 and a plurality of bandages 104 (shown in phantom in FIG. 8). Each bandage 104 includes graphic image 106 and outer edge 108. Sheet 102 and bandages 104 have substantially the same features and attributes as sheet 22 and bandages 24, and sheet 71 and bandages 72, as previously described in association with FIGS. 1–4, and 5–7, respectively. For example, bandage 104 includes non-adhesive side 117 and adhesive side 118 (FIG. 9–10).

Cover 110 includes body 111, outer edge 112 and inner edge 114. Cover 110 is positioned over edge 108 of bandage 104 to seal edge 108 of bandage 104. Inner edge 114 defines aperture 116 so that non-adhesive side 117 of bandage 104 is partially exposed to receive printing of image 106 on bandage 104. Image 106 can be placed anywhere along the exposed portions of non-adhesive side 117.

Bandages 104 are further illustrated in FIG. 9, which is a section view of bandage 104 of FIG. 8. As shown in FIG. 9, at opposite ends of bandage 104, outer edge 112 of cover 110 is removably secured as a sealed seam against sheet 102 and inner edge 114 of cover 110 is removably secured as a sealed seam against non-adhesive side 117 of bandage 104. As shown in FIG. 10, outer edge 112 of cover 110 is also removably secured as a sealed seam against sheet 102 and inner edge 114 of cover 110 is also removably secured as a sealed seam against non-adhesive side 117 of bandage 104. This combination of sealed seams defined by inner edge 114 and outer edge 112 of cover 110 effectively seals edge 108 of bandage 104 against sheet 102, thereby protecting bandage 104, particularly pad 119, from intrusion of germs, dust, etc. At the same time, aperture 116 of cover 110 permits printing of images 106 onto partially exposed non-adhesive side 117 of bandage 104 when system 100 is fed through a printer for printing images 106 onto bandage(s) 104.

Figure 11:
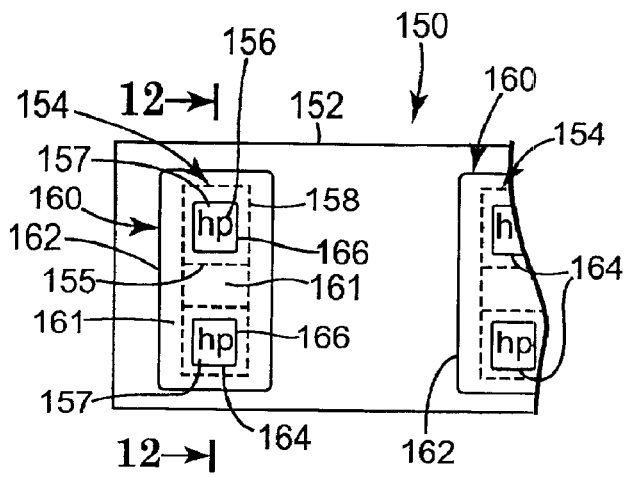
FIG. 11 is a plan view of a sheet of printable bandages, according to an embodiment of the present invention.
Figure 12:
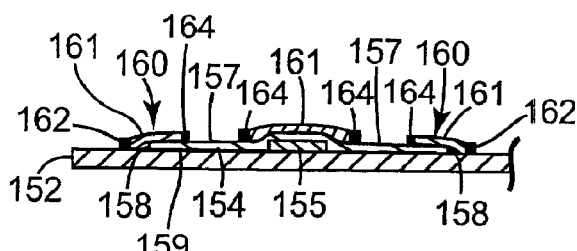
FIG. 12 is a sectional view of FIG. 11 as taken along lines 12—12, according to an embodiment of the present invention.

FIGS. 11–12 illustrate printable bandage system 150 of the present invention including cover 160. As shown in FIG. 11, printable bandage system 150 includes sheet 152, at least one bandage 154 (shown in phantom in FIG. 11), and cover 160. Bandage 154 includes pad 155, printed graphic image 156, and edge 158. Sheet 152 and bandages 154 have substantially the same features and attributes as sheet 22 and bandages 24, sheet 71 and bandages 72, and sheet 102 and bandages 104, as previously described in association with FIGS. 1–10. For example, bandage 154 includes non-adhesive side 157 and adhesive side 159 (FIGS. 11–12).

Cover 160 includes body 161, outer edge 162, and inner edge 164. Inner edge 164 defines aperture 166. Cover 160 has substantially the same features and attributes as cover 110, as previously described in association with FIGS. 8–10. However, cover 160 includes a pair of apertures 166 instead of a single aperture 116, as in cover 110. In this embodiment, cover 160 extends over both edge 158 of bandage 154 and directly over pad 155 of bandage 154. This leaves the remainder of bandage 154, commonly known as securing strips, exposed as a printable portion to receive printing of image 156 from a printer, such as printer 32.

Bandage 154 is further illustrated in FIG. 12, which is a sectional view of FIG. 11. As shown in FIG. 11, at opposite ends of bandage 154, outer edge 162 of cover 160 is removably secured as a sealed seam against sheet 152 and inner edge 164 of cover 160 is removably secured as sealed seam against non-adhesive side 157 of bandage 154. This combination of sealed seams defined by inner edge 164 and outer edge 162 of cover 160 effectively seals edge 158 of bandage 154 against sheet 152, thereby protecting bandage 154, particularly pad 155, from intrusion of germs, dust, etc.

Figure 13:
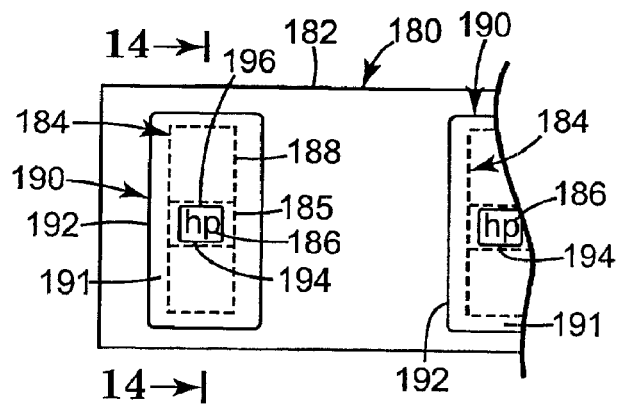
FIG. 13 is a plan view of a sheet of printable bandages, according to an embodiment of the present invention.
Figure 14:
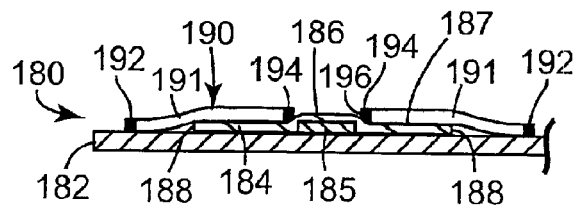
FIG. 14 is a sectional view of FIG. 13 as taken along lines 14—14, according to an embodiment of the present invention.

As shown in FIGS. 13–14, printable bandage system 180 of the present invention includes sheet 182 and at least one bandage 184 (shown in phantom in FIG. 13) including pad 185, printed graphic image 186 and edge 188. Cover 190 includes body 191, outer edge 192, and inner edge 194 defining aperture 196. Cover 190 has substantially the same features and attributes as covers 110 and 160, as previously described in association with FIGS. 8–12. However, cover 190 includes single aperture 196, as cover 110 has single aperture 116. In this embodiment, cover 190 extends over edge 188 and the edges of pad 185 of bandage 184. Aperture 196 leaves an area of non-adhesive side 187 of bandage 184, which corresponds to the location of pad 185, exposed as a printable portion to receive printing of image 186 from a printer.

FIG. 14 is a sectional view of bandage system 180 of FIG. 13. As shown in FIG. 14, outer edge 192 of cover 190 is removably secured as a sealed seam against sheet 182 and inner edge 194 of cover 190 is removably secured as a sealed seam against non-adhesive side 187 of bandage 184. This combination of sealed seams defined by inner edge 194 and outer edge 192 of cover 190 effectively seals edge 188 of bandage 184 against sheet 182, thereby protecting bandage 184 from intrusion of germs, dust, etc.

A system and method for printing images on bandages has numerous advantageous features. Foremost, one can print any desired image on a bandage by feeding a sheet of bandages through a printer. The consumer is no longer limited to purchasing bandages with previously printed images, such as Mickey Mouse® characters, from a retail store. Rather, the consumer can print any custom graphic image of their choosing on one or more bandages. In addition, the sheet of printable bandages includes an optional protective cover for maintaining the sterility and/or cleanliness of the bandages before, during, and after printing of the images on the bandages. The protective cover can alternatively cover the edges of bandages, the pad, the non-adhesive backing portions of the bandages, or any combination thereof, so that a desired portion of the bandage is exposed for printing of the images on the bandage while covering other portions of the bandage.

While specific embodiments have been illustrated and described herein for purposes of description of the preferred embodiment, it will be appreciated by those of ordinary skill in the art that a wide variety of alternate and/or equivalent implementations may be substituted for the specific embodiments shown and described without departing from the scope of the present invention. Those with skill in the chemical, mechanical, electro-mechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A printable bandage system comprising:
   a non-stick sheet; and
   a bandage removably secured to the non-stick sheet, the bandage including an outer edge, a first adhesive side and a second non-adhesive side, the first adhesive side including a pad and being removably secured to the non-stick sheet and the second non-adhesive side including a printable portion configured to receive the printing of an image thereon; and
   a protective cover including a body, an inner edge, and an outer edge with the inner edge of the cover removably sealed against the second non-adhesive side of the bandage, the body of the cover extending over the substantially the entire outer edge of the bandage, the outer edge of the cover removably sealed against the non-stick sheet, and the inner edge of the cover defining an aperture exposing the printable portion of the second non-adhesive side of the bandage to enable printing of an image on the printable portion through the aperture.

2. The bandage system of claim 1, wherein the non-stick sheet includes a plurality of separable portions joined by perforated seams,
   wherein the system further comprises a plurality of bandages, including the bandage, with each bandage removably secured to a corresponding separable portion of the non-stick sheet and each bandage including an outer edge, a first adhesive side and a second non-adhesive side, the first adhesive side including a pad and being removably secured to the non-stick sheet and the second non-adhesive side including a printable portion configured to receive the printing of an image thereon,
   wherein the system further comprising a plurality of protective covers, including the protective cover, with each protective cover including an inner edge, an outer edge, and a body, the inner edge of each cover removably sealed against the second non-adhesive side of each bandage, the body of each cover extending over the substantially the entire outer edge of each bandage, the outer edge of each cover removably sealed against the non-stick sheet, and the inner edge of each cover defining an aperture exposing the printable portion of the second non-adhesive side of each bandage to enable printing of an image on the printable portion of each bandage through the aperture.

3. The bandage system of claim 1, wherein the bandage includes a pair of securing portions extending outwardly from opposite sides of the pad, and the aperture of the cover is sized and shaped to generally cover the securing portions while generally exposing only a first portion of the second non-adhesive side, generally corresponding to a location of the pad of the bandage, to enable printing of the image on the first portion through the aperture.

4. The bandage system of claim 1, wherein the bandage includes a pair of securing portions extending outwardly from opposite sides of the pad, and the aperture of the cover is sized and shaped to expose both a first portion of the second non-adhesive side, generally corresponding to a location of the pad of the bandage, and the securing portions of the second non-adhesive side of the bandage to enable printing of the image on the first portion and the securing portions through the aperture.

5. The bandage system of claim 1, wherein the bandage includes a pair of securing portions extending outwardly from opposite sides of the pad, and the aperture of the cover is sized and shaped to generally cover a first portion of the second non-adhesive side generally corresponding to the pad and to generally expose the securing portions of the second non-adhesive side of the bandage to enable printing of the image on the exposed securing portions through the aperture.

6. A printable bandage system comprising:
   a non-stick sheet including a plurality of separable portions; and
   a plurality of bandages removably secured to the non-stick sheet in a generally parallel, spaced arrangement with one bandage disposed on each separable portion of the non-stick sheet, each bandage including a centrally located pad and a pair of securing portions extending outwardly from opposite sides of the pad, each bandage defining a first adhesive side and a second non-adhesive side with the pad being fixed on the first adhesive side of the bandage, and the first adhesive side being removably secured to the non-stick sheet; and
   a protective cover including a generally rectangular-shaped body and an outer edge, the body sized, shaped, and positioned so that the outer edge of the cover extends across the plurality of bandages so that the outer edge of the cover generally encompasses the pad of each bandage, the outer edge of the cover removably sealed against both the second non-adhesive side of the bandage and the non-stick sheet between the spaced bandages, thereby exposing the securing portions of the second non-adhesive side of each bandage for printing of an image on the exposed securing portions while maintaining sterility of the pad.

7. A bandage system comprising:

a non-stick sheet;

a bandage having a pad portion and a pair of securing strips extending outwardly from opposite sides of the pad portion, with each securing strip comprising a non-adhesive side and an adhesive side wherein the adhesive side is removably secured to the non-stick sheet, and a protective cover extending over an outer edge of the bandage and having an outer edge removably secured against the non-stick sheet and an at least one inner edge defining a removable seal in contact against at least one of the pad portion and the non-adhesive side of the securing strips to protect a periphery of the pad portion, wherein the at least one inner edge defines an aperture in the protective cover to expose a portion of the bandage.

8. The bandage system of claim 7, wherein the at least one inner edge of the protective cover is shaped and sized to enable the removable seal to be in contact against only the securing strips.

9. The bandage system of claim 7, wherein the at least one inner edge of the protective cover is shaped and sized to enable the removable seal to be in contact against only the pad portion.

10. The bandage system of claim 7, wherein the at least one inner edge of the protective cover is shaped and sized to enable the removable seal to be in contact against both the pad portion and the securing strips.

* * * * *

UNITED STATES PATENT AND TRADEMARK OFFICE
CERTIFICATE OF CORRECTION

PATENT NO. : 6,924,411 B2  
DATED : August 2, 2005  
INVENTOR(S) : Reider

It is certified that error appears in the above-identified patent and that said Letters Patent is hereby corrected as shown below:

Column 5,
Line 61, after "over", delete "the".

Signed and Sealed this

Thirteenth Day of December, 2005

JON W. DUDAS  
*Director of the United States Patent and Trademark Office*